(12) United States Patent
Campos et al.

(10) Patent No.: US 6,670,490 B1
(45) Date of Patent: Dec. 30, 2003

(54) PLATINUM-RHENIUM-TIN CATALYST FOR HYDROGENATION IN AQUEOUS SOLUTION

(75) Inventors: Daniel Campos, Lancaster, PA (US); Gregg Mason Sisler, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/327,795

(22) Filed: Dec. 23, 2002

(51) Int. Cl.⁷ .................. C07D 307/08; C07C 29/149
(52) U.S. Cl. ................. 549/508; 568/864; 502/185
(58) Field of Search .................. 549/508; 568/864; 502/185

(56) References Cited

U.S. PATENT DOCUMENTS

| | | |
|---|---|---|
| 4,333,857 A | 6/1982 | Lim et al. |
| 5,214,012 A | 5/1993 | Suzuki et al. |
| 5,369,069 A | 11/1994 | Suzuki et al. |
| 5,478,952 A | 12/1995 | Schwartz |
| 5,698,749 A | 12/1997 | Pedersen et al. |
| 5,958,819 A | 9/1999 | Johnson et al. |
| 6,008,384 A | 12/1999 | Bockrath et al. |
| 6,214,211 B1 | 4/2001 | Itoh |
| 6,303,531 B1 | 10/2001 | Lussier et al. |

FOREIGN PATENT DOCUMENTS

| | | |
|---|---|---|
| CN | 1031029 | 2/1989 |
| CN | 1031489 | 3/1989 |
| CN | 1030326 | 11/1995 |
| CN | 1030376 | 11/1995 |
| CN | 1048427 | 1/2000 |
| CN | 1240813 | 1/2000 |
| CN | 1056869 | 9/2000 |
| CN | 1060204 | 1/2001 |
| CN | 1060755 | 1/2001 |
| CN | 1069682 | 8/2001 |
| CN | 1313268 | 9/2001 |
| CN | 1353012 | 6/2002 |
| JP | HEI 5-246915 A | 9/1993 |
| JP | 6127936 | 5/1994 |

OTHER PUBLICATIONS

Junichi Kanetaka, Seiichi Kiryu, Taisuke Asano, Shinobu Masamyne, "Hydrogenation of Maleic Anhydride and Intermediates by Nickel–Rhenium Catalyst Supported on Kieselguhr," Bulletin of The Japan Petroleum Institute, May 1970, vol. 12.

*Primary Examiner*—Taofiq Solola

(57) ABSTRACT

An improved catalyst of platinum, rhenium and tin with an inert support used for hydrogenation of an hydrogenatable precursor in an aqueous solution and a method for using the catalyst in the production of tetrahydrofuran and 1,4-butanediol from such a hydrogenatable precursor in an aqueous solution.

12 Claims, No Drawings

PLATINUM-RHENIUM-TIN CATALYST FOR HYDROGENATION IN AQUEOUS SOLUTION

BACKGROUND OF THE INVENTION

1. Field of the Invention

This invention relates to a catalyst with an inert support for hydrogenation in an aqueous solution and a method for using the catalyst in the production of tetrahydrofuran and 1,4-butanediol from a hydrogenatable precursor in an aqueous solution.

2. Description of the Related Art

Various methods and reaction systems have been proposed in the past for manufacturing tetrahydrofuran (THF) and 1,4 butanediol (BDO) by catalytic hydrogenation of gamma butyrolactone (GBL), maleic acid (MAC), maleic anhydride (MAN), succinic acid (SAC) or related hydrogenatable precursors. Also, a variety of hydrogenation catalysts have been historically proposed for this purpose, including various transition metals and their combinations deposited on various inert supports, all as generally known in the art. Many of these catalysts are proposed for use in hydrogenations carried out in an organic solvent or organic reaction media and not in an aqueous solution phase. At least one prior publication suggests that water and succinic acid may be considered as inhibitors to the desired catalysis, see Bulletin of Japan Petroleum Institute, Volume 12, pages 89 to 96 (1970).

A laid-open Japanese patent application (Kokai) 5-246915 for the aqueous phase catalytic hydrogenation of an organic carboxylic acid or ester teaches the use of any Group VIII noble metal, optionally in combination with either tin, rhenium or germanium, on a defined activated carbon support.

U.S. Pat. No. 5,698,749 discloses a process for producing 1,4-butanediol by aqueous hydrogenation of a hydrogenatable precursor using a catalyst comprised of a noble metal of Group VIII and at least one of rhenium, tungsten and molybdenum on a carbon support pretreated with an oxidizing agent.

In U.S. Pat. No. 5,478,952 a highly effective catalyst for aqueous phase hydrogenations is disclosed. This catalyst consists of ruthenium and rhenium wherein both metal components are present in a highly dispersed reduced state on a carbon support which is characterized by a BET surface area of less than 2,000 $m^2/g$.

U.S. Pat. No. 6,008,384 discloses a catalyst of highly dispersed, reduced Ru and Re in the presence of Sn on a carbon support used for an improved hydrogenation process for the production of tetrahydrofuran, gamma butyrolactone, 1,4-butanediol and the like from a hydrogenatable precursor such as maleic acid, succinic acid, corresponding esters and their mixtures and the like in an aqueous solution in the presence of hydrogen. This patent is incorporated herein by way of reference.

SUMMARY OF THE INVENTION

This invention is hydrogenation catalyst comprising about 0.5% to 3% platinum, about 1% to 10% rhenium and about 0.1% to about 5% tin supported on carbon, wherein the percentages are by total weight of the supported catalyst.

This invention is also a method for making tetrahydrofuran, 1,4-butanediol or mixtures thereof by hydrogenating a hydrogenatable precursor in a reactor in the presence of a catalyst comprising about 0.5% to 3% platinum, about 1% to 10% rhenium and about 0.1% to 5% tin, supported on carbon, wherein the percentages are by total weight of supported catalyst.

DETAILED DESCRIPTION OF THE INVENTION

This invention is a novel trimetallic platinum-rhenium-tin catalyst that exhibits certain advantages when employed during hydrogenation of a hydrogenatable precursor in an aqueous solution. The invention is also an improved process or method for making tetrahydrofuran, 1,4-butanediol or mixtures thereof by hydrogenating a hydrogenatable precursor such as gamma butyrolactone, maleic anhydride, maleic acid, succinic acid, or mixtures thereof. As such, the trimetallic catalyst of this invention and the process of using this catalyst may be viewed as an improvement of the bimetallic ruthenium-rhenium carbon-supported catalyst of U.S. Pat. No. 5,478,952 and of the trimetallic ruthenium-rhenium-tin carbon-supported catalyst of U.S. Pat. No. 6,008,384.

This catalyst composition results in the conversion of a hydrogenatable precursor in an aqueous solution at high conversion rates for an extended period of time consistent with large-scale commercial operations and with significantly lower over-hydrogenation. Moreover, it has been discovered that the addition of tin to a platinum and rhenium catalyst leads to an improved control of selectivity among the more useful products, such as tetrahydrofuran and 1,4-butanediol. Concurrently, reduced relative production of undesirable by-products, such as n-butanol, n-propanol and volatile hydrocarbons, such as methane, ethane, propane and butane has been discovered. Although not confining possible explanation for this discovery to any single rationale or theory, it is currently believed that the addition of relatively small amounts of tin moderates the high catalytic activity of the platinum-rhenium catalyst and the overall rate of hydrogenation so as to improve selectivity to the desired products. This results in a superior yield of desired products and control of the ratio of tetrahydrofuran to by-products being produced without significantly promoting over-hydrogenation and production of undesirable by-products.

Consistent with this view, the respective lower limit or minimum loading of platinum and rhenium metals relative to the carbon support is somewhat higher than it would be for the bimetallic catalyst without tin in order to at least partially compensate for the presence of tin. Thus, the trimetallic catalyst comprises at least 0.5% by weight of platinum metal and at least 1% of rhenium metal relative to the combined weight of metals and inert support. The upper limit of the platinum and rhenium metal will be about 3% platinum and about 10% rhenium on the same basis. It should be appreciated that concentrations of platinum and rhenium in excess of these upper limits may be operative and as such should be considered equivalent for purposes of the present invention. However, such concentrations are believed to offer little advantage in terms of convenience and/or cost.

Thus, the present invention provides an improved hydrogenation catalyst of about 0.5% to 3% platinum, about 1% to 10% rhenium, and about 0.1 to 1.0% tin, supported on carbon, wherein the percentages are by total weight of supported catalyst and wherein the carbon support is characterized by a BET surface area of less than 2,000 $m^2/g$. Preferably, the catalyst composition is about 0.8% to 2% platinum, about 3% to 8% rhenium, and about 0.1% to 1.5% tin, supported on the aforementioned carbon, wherein the percentages are by total weight of the supported catalyst.

The carbon useful as a catalyst support in the present invention is preferably a porous particulate solid characterized by a size distribution typically ranging from about 5 to 100 micrometers for slurry applications and from about 0.8 to 4 millimeters (mm) for fixed bed applications and a BET surface area typically ranging from a few hundred to nearly 2,000 m$^2$/g. Preferably, the carbon support material is a commercially available material having an average particle size of about 20 micrometers for slurry applications and about 3 mm for fixed bed applications and a BET surface area from about 700 to about 1,600 m$^2$/g. The catalyst support can be manufactured to have a latent acid, a neutral, or a basic pH. Optionally, the catalyst support can be treated prior to metal deposition by one or more techniques as generally known in the art, such as, impregnation with alkali metal salts and/or calcination or acid wash. Examples of suitable carbon supports are SX-2 and Darco KBB carbons, supplied by Norit Americas Inc., with BET surface areas of 700 and 1,500 m$^2$/g, respectively.

The method of preparing the catalyst of the present invention can be generally any such process as known in the art, provided that the desired composition of metals and inert support is achieved. One such method is to prepare a water solution of a soluble platinum compound, a soluble rhenium compound and a soluble tin compound and then add this solution to the carbon support. The method of adding the solution to the support can be any technique generally known in the art including by way of example, but not by way of limitation: immersion, spraying, incipient wetness, or the like. The water is evaporated, thereby depositing the platinum, rhenium and tin compounds on the carbon support. The dry or partially dried composite material is then added to water to form an aqueous slurry and the slurry is then subjected to a reducing atmosphere at elevated temperature for a time sufficient to reduce the platinum, rhenium and tin. The aqueous catalyst slurry can then be added to the reaction zone for use as a catalyst. Alternatively, the aqueous catalyst slurry can be dried or partially dried and then used as a catalyst. Optionally, after the deposition step, the dry or partially dried composite material can be subjected to a reducing atmosphere at an elevated temperature (150 to 270° C.) while in a solid state and then used as catalyst.

A second method related to the above is to perform the process entirely in the presence of water or the aqueous solution of the hydrogenatable precursor. In this technique, the water solutions of the platinum, rhenium and tin compounds are commingled with the carbon support while subjected to a reducing atmosphere at an elevated temperature (150 to 270° C.). This methodology is of particular value and commercial interest in that the catalyst drying steps are eliminated, and that the co-depositing and co-reduction can be literally performed in situ in the hydrogenation reactor and can even be accomplished in the presence of reactants such as, maleic acid, succinic acid and/or gamma butyrolactone.

A third method of producing the catalyst is to sequentially deposit, dry and reduce the platinum and rhenium on the carbon support, then add the solution of the tin compound, and deposit, dry and reduce it at an elevated temperature on the same support. Either or both reduction steps are performed in a reducing atmosphere and at the elevated temperature of 150 to 270° C. and may be performed dry or in an aqueous slurry. Preferentially, both reduction steps are performed in an aqueous slurry.

It should be further appreciated that various other methods or alternate modes of depositing the platinum, rhenium and tin compounds on the carbon support, such as by selective precipitation and the like (optionally, with or without solvent washing) to selectively remove less desirable companion anions are contemplated as being equivalent methodologies for use in preparing the catalyst of the present invention. This would also include the simultaneous or various sequential depositions of the individual metal components.

The metallic compounds useful in the present invention for preparing the catalyst can be generally any such compound that is either water soluble or partially water soluble or can be readily converted to a water soluble or partially water soluble compound that can be deposited on the carbon support. This would include by way of example, but not by way of limitation, such platinum compounds as chloroplatinic acid, ammonium chloroplatinate, bromoplatinic acid, platinum trichloride, platinum tetrachloride hydrate, platinum dichlorocarbonyl dichloride, dinitrodiaminoplatinum, sodium tetranitroplatinate and the like. This would also include by way of example, but not by way of limitation, such rhenium compounds as ammonium perrhenate, sodium perrhenate, potassium perrhenate, rhenium heptoxide and the like. This would further include by way of example, but not by way of limitation, such tin compounds as potassium stannate, sodium stannate, stannic chloride, stannous chloride, stannous nitrate, stannous oxalate and the like. Typically, sodium stannate or stannic chloride is used because of availability and cost.

The reducing agent used for the previously described catalyst reduction step can generally be any reductant or reducing environment consistent with either liquid phase reduction or vapor phase reduction including by way of example, but not by way of limitation: formaldehyde, hydrazine hydrate, hydroxylamine, sodium hypophosphite, sodium formate, glucose, acetaldehyde, sodium borohydride, hydrogen and the like. When a vapor phase reduction is employed involving gaseous hydrogen (with or without an inert diluent gas, such as nitrogen) in the presence of the catalyst precursor, typically the vapor phase reduction is performed at a temperature range of 100 to 500° C., preferably 250 to 300° C., from atmospheric pressure up to about 3000 psig ($2.07 \times 10^7$ Pa gage).

The present invention is also the use of this catalyst for the catalytic hydrogenation of a hydrogenatable precursor in an aqueous solution comprising the steps of:

(a) hydrogenating a hydrogenatable precursor in an aqueous solution in the presence of hydrogen and a catalyst of the above composition, and, (b) recovering at least one hydrogenated product.

More specifically, this invention is a method for making tetrahydrofuran, 1,4-butanediol or mixtures thereof by hydrogenating a hydrogenatable precursor in the presence of a catalyst comprising about 0.5% to 3% platinum, about 1% to 10% rhenium and about 0.1 to 1.0% tin, supported on carbon, wherein the percentages are by total weight of the supported catalyst. The catalyst is characterized by a space-time yield (STY) for conversion of maleic acid to tetrahydrofuran in excess of 700 grams of product per kilogram of catalyst per hour initially and 600 grams of product per kilogram of catalyst per hour after 200 hours of operation at 250° C. and 2,000 psig ($14 \times 10^6$ Pa gage) pressure. Typically, the preferred temperature for the hydrogenation step is from 150 to about 260° C.

For purposes of the present invention, a hydrogenatable precursor can be, broadly, any compound or material that can be chemically reduced by hydrogenation or hydrogen uptake to yield the desired products. This would include, but not by way of limitation, various organic compounds containing unsaturation or oxygenated functional groups or both. Most particularly, the aqueous phase catalytic reduction of maleic acid to gamma butyrolactone, 1,4-butanediol and tetrahydrofuran is illustrative of the utility of the method according to the present invention. In this regard, and as illustrated in the examples, it should be appreciated that various products of the sequential hydrogenation reaction are also potential hydrogenatable precursors. That is, in the conversion of maleic acid to tetrahydrofuran, the chemical reduction is known to be sequential. This involves the rapid addition of hydrogen across the double bond thereby converting maleic acid to succinic acid, followed by the slower addition of hydrogen-forming potential intermediates such as gamma butyrolactone and/or 1,4-butanediol and ultimately, tetrahydrofuran (corresponding to the uptake of 5 moles of $H_2$ and production of three moles of $H_2O$ per mole of THF). In commercial production, the overall selectivity to THF production can be significantly influenced by optimizing reaction conditions; including maintaining adequate acidity so as to favor ring closure and cyclic ether production at the expense of diol production, continuous vapor removal of the more volatile products, and subsequent separation and recycle of the lactone. In these cases, the gamma butyrolactone can be viewed as either a co-product or as a recycled hydrogenatable precursor reactant.

The method of using the inventive catalyst to hydrogenate a hydrogenatable precursor according to the present invention can be performed by various modes of operation as generally known in the art. Thus, the overall hydrogenation process can be performed with a fixed bed reactor, various types of agitated slurry reactors, either gas or mechanically agitated, or the like. The hydrogenation process can be operated in either a batch or continuous mode, wherein an aqueous liquid phase containing the hydrogenatable precursor is in contact with a gaseous phase containing hydrogen at elevated pressure and the particulate solid catalyst. Typically, such hydrogenation reactions are performed at temperatures from about 100° C. to about 300° C. in sealed reactors maintained at pressures from about 1000 to about 3000 psig ($7 \times 10^6$ to about $21 \times 10^6$ Pa gage).

When the trimetallic platinum-rhenium-tin catalyst of the present invention is used to produce 1,4-butanediol and tetrahydrofuran at a desired or controlled molar ratio, the hydrogenation is preferably performed at a temperature above about 150° C. and below about 260° C. To obtain a high 1,4-butanediol to tetrahydrofuran (BDO/THF) molar ratio, the hydrogenation to those desired products should advantageously be performed at or near the lower end of this temperature range. The method and conditions used as the mode of operation will also advantageously influence the BDO/THF molar ratio during hydrogenation. For example, the liquid phase removal of products from the hydrogenation reactor will tend to enhance and maximize 1,4-butanediol production rather than tetrahydrofuran. In contrast, continuous vapor removal of product from the hydrogenation reactor will tend to maximize tetrahydrofuran production at the expense of 1,4-butanediol. Thus, as a practical consideration, low temperature liquid product removal intended to optimize 1,4-butanediol production favors the use of fixed bed catalytic reactors. On the other hand, high temperature vapor phase product removal intended to optimize tetrahydrofuran production favors the use of a slurry or stirred reactor.

The following examples are presented to more fully demonstrate and further illustrate various individual aspects and features of the present invention while the comparative examples are intended to further illustrate the differences and advantages of the present invention. As such, the examples are meant to illustrate the invention but are not meant to be limiting in any way.

EXAMPLES

The examples given below measure the relative performance of different catalyst compositions. For comparison purposes, in each of these tests the catalyst metals, the carbon support, and the reactants were mixed together in an aqueous system and the hydrogenation reaction was carried out using a fixed procedure. It is understood that alternate procedures for preparing the catalyst and carrying out the hydrogenation reaction may also be used, as described previously. Because a single reaction temperature was chosen for comparison purposes, and because the chosen temperature (250° C.) was toward the high end of the previously described preferred range (150 to 260° C.), the proportion of THF relative to BDO was favored in all these examples. For most of the following examples, about 70% to 85% of the desired two products was THF, with BDO as the remainder. The development of alternate procedures for a particular hydrogenatable precursor and to obtain a particularly desired product composition ratio will be apparent to one skilled in the art and need not involve extensive experimentation Examples 1–4

The catalysts were prepared in-situ and tested simultaneously by adding to a 300-cc autoclave 0.4 g 1% platinum/carbon precursor obtained from Aldrich (cat. #20,592–3) and given amounts of $Re_2O_5$ and $SnCl_4$ (as applicable) to give the catalyst compositions given in Table 1. Also, 125 g of 20% aqueous GBL was added to the autoclave as the test solution. The autoclave was heated to 250° C. and then pressurized to 2000 psig ($14 \times 10^6$ Pa gage) with $H_2$, while stirring. The conditions were maintained for 45 min, after which it was rapidly cooled down and the products were analyzed by GC (gas chromatography) to determine the net molar production rate (STY), and molar selectivity. The results are shown in Table 1.

The STY and Selectivity are defined as follows:

STY=mol/Kg of catalyst-hr

Molar Selectivity=(THF+BDO)STY/[(THF+BDO)STY+By-products STY]

By-products=propanol+butanol+propionic acid+butyric acid

TABLE 1

| Ex. | Catalyst % on C | THF+BDO STY | Molar Selectivity THF+BDO |
|---|---|---|---|
| A | 1% Pt | 11.2 | 0.65 |
| B | 1% Pt,1% Re | 23.9 | 0.79 |
| C | 1% Pt,3% Re | 41.2 | 0.84 |
| D | 1% Pt,4% Re | 45.1 | 0.85 |
| E | 1% Pt,5% Re | 55.7 | 0.87 |
| 1 | 1% Pt,3% Re,0.2% Sn | 33.0 | 0.90 |
| 2 | 1% Pt,3% Re,04% Sn | 40.7 | 0.90 |
| 3 | 1% Pt,3% Re,0.6% Sn | 26.9 | 0.91 |
| 4 | 1% Pt,3% Re,0.8% Sn | 40.0 | 0.91 |
| F | 1% Pt,0.8% Sn | 28.8 | 0.92 |

It can be observed from Table 1 that although adding rhenium to a platinum-carbon catalyst increases the catalytic activity and selectivity, the selectivity is further increased by the addition of tin.

Example 5

The catalyst of the example was prepared by impregnating aqueous $Re_2O_5$ and $SnCl_4$ on 1% platinum/carbon precursor obtained from Aldrich (cat. #20,592–3). Then 6.5 grams on dry basis of a catalyst composition of 1% platinum, 6% rhenium, 0.8% tin was loaded in a continuous bubble column reactor to measure activity and selectivity. The comparative examples were prepared similarly, except for the composition.

The continuous bubble column reactor consisted of a vertical Hastelloy C pipe, ¾ inch I.D. by 41.5 inches long (2 cm I.D. by 105 cm long) with multiple ports for loading catalyst and reactants and removing products. The reactor was heated continuously and held at 250 degrees C and maintained at a pressure of 2,000 psi ($1.38 \times 10^7$ Pa) with a constant hydrogen flow. The feed solution was aqueous 30% maleic acid and was fed at about 22 to 25 cm³/hr. Hydrogen was bubbled through the reactor at 1100 sccm (standard cubic centimeters per minute) to provide the agitation to slurry the catalyst and to sweep THF, by-products and water from the reactor in the vapor phase.

Table 2 shows data on the inventive platinum-rhenium-tin catalyst opposite Comparative Example catalysts run in the reactor under similar conditions.

Peak THF STY and THF STY at 200 hours were measured as grams THF/kg catalyst/hr. Useful Selectivity at 200 hours was measured as the quantity (carbon in THF, GBL, BDO and SAC in product) divided by the quantity (all carbon collected in product). Deactivation Rate was measured over hours 100 to 200 in terms of THF STY/day.

TABLE 2

| Example | Catalyst (% on carbon) | Peak THF STY | THF STY at 200 hrs | Useful Selectivity at 200 hrs | Deactivation Rate |
|---|---|---|---|---|---|
| 5 | 1% Pt, 6% Re, 0.8% Sn | 740 | 600 | 94% | 16 |
| G | 1% Ru, 6% Re | 415 | 200 | 89% | 24 |
| H | 2% Ru, 6% Re, 0.9% Sn | 760 | 400 | 91% | 31 |

The platinum-rhenium-tin catalyst clearly showed a selectivity advantage of several percent over the ruthenium-rhenium and the ruthenium-rhenium-tin catalysts. Also, the platinum-rhenium-tin catalyst had initial activity comparable to the ruthenium-rhenium-tin catalyst, but it retained more of that activity as the run continued as indicated by the lower deactivation rate and the higher THF STY at the 200 hour mark.

We claim:

1. A hydrogenation catalyst comprising about 0.5% to 3% platinum, about 1% to 10% rhenium and about 0.1% to about 5% tin supported on carbon, wherein the percentages are by total weight of the supported catalyst.

2. The catalyst of claim 1, comprising about 0.8% to 2% platinum and about 3% to 8% rhenium.

3. The catalyst of claim 1, wherein the carbon catalyst support is characterized by a BET surface area of less than 2,000 m²/g.

4. A method for making tetrahydrofuran, 1,4-butanediol or mixtures thereof by hydrogenating a hydrogenatable precursor in a reactor in the presence of a catalyst comprising about 0.5% to 3% platinum, about 1% to 10% rhenium and about 0.1% to 5% tin, supported on carbon, wherein the percentages are by total weight of supported catalyst.

5. The method of claim 4, wherein the catalyst comprises about 0.8% to 2% platinum and about 3% to 8% rhenium.

6. The method of claim 4, wherein the temperature for the hydrogenation is from 150 to 260 degrees C.

7. The method of claim 4, wherein 1,4-butanediol is predominantly produced at a temperature of 150 to 225 degrees C. and the 1,4-butanediol is removed from the reactor as a liquid.

8. The method of claim 4, wherein tetrahydrofuran is predominantly produced at a temperature of 225 to 260 degrees C. and the tetrahydrofuran is removed from the reactor as a vapor.

9. The method of claim 4, wherein the hydrogenatable precursor is selected from the group consisting of maleic acid, maleic anhydride, fumaric acid, succinic acid, the esters corresponding to these acids, gamma butyrolactone and mixtures thereof.

10. The method of claim 4, wherein the catalyst is prepared by slurrying a platinum-carbon catalyst composition in an aqueous solution with a water-soluble rhenium compound and a water-soluble tin compound.

11. The method of claim 4, wherein the catalyst is prepared by slurrying a platinum-carbon catalyst composition in an aqueous solution of a hydrogenatable precursor with a water-soluble rhenium compound, and a water-soluble tin compound.

12. The method of claim 10 or 11, wherein the hydrogenatable precursor is hydrogenated at 200 to 260° C. and 1000 to 2500 psig total pressure for a holding period of 1 to 24 hours.

* * * * *